United States Patent
Dall'Oglio

(10) Patent No.: US 10,980,627 B2
(45) Date of Patent: Apr. 20, 2021

(54) DEVICE FOR THE TREATMENT OF ESOPHAGEAL STENOSES

(71) Applicants: SIDAM S.R.L., Frazione San Giacomo Roncole (IT); OSPEDALE PEDIATRICO BAMBINO GESU', Rome (IT); EVOLUZIONE S.R.L., Rome (IT)

(72) Inventor: Luigi Dall'Oglio, Rome (IT)

(73) Assignees: Sidam S.r.l., Frazione San Giacomo Roncole (IT); Ospedale Pediatrico Bambino Gesu', Rome (IT); Evoluzione S.r.l., Rome (IT)

( * ) Notice: Subject to any disclaimer, the term of this patent is extended or adjusted under 35 U.S.C. 154(b) by 681 days.

(21) Appl. No.: 15/316,805

(22) PCT Filed: Jun. 4, 2015

(86) PCT No.: PCT/IB2015/054242
§ 371 (c)(1),
(2) Date: Dec. 6, 2016

(87) PCT Pub. No.: WO2015/186097
PCT Pub. Date: Dec. 10, 2015

(65) Prior Publication Data
US 2017/0156841 A1    Jun. 8, 2017

(30) Foreign Application Priority Data

Jun. 6, 2014 (IT) .......................... MO2014A000166

(51) Int. Cl.
*A61F 2/04* (2013.01)
*A61M 25/00* (2006.01)
(Continued)

(52) U.S. Cl.
CPC ............. *A61F 2/04* (2013.01); *A61M 25/005* (2013.01); *A61M 25/0043* (2013.01);
(Continued)

(58) Field of Classification Search
CPC . A61F 2/04; A61F 2002/044; A61M 25/0043; A61M 29/02; A61M 29/00;
(Continued)

(56) References Cited

U.S. PATENT DOCUMENTS

| 2005/0245894 A1 | 11/2005 | Zadno-Azizi |
| 2006/0135981 A1 | 6/2006 | Lenker et al. |

(Continued)

FOREIGN PATENT DOCUMENTS

| WO | 96/29014 A1 | 9/1996 | |
| WO | 2012/061657 A2 | 5/2012 | |
| WO | WO 2012110891 A1 * | 8/2012 | ............ A61M 29/00 |

OTHER PUBLICATIONS

European Search Report dated Feb. 5, 2015 from Italian Patent Application No. MO2014A000166 filed Jun. 6, 2014.
(Continued)

*Primary Examiner* — Jerrah Edwards
*Assistant Examiner* — Rokhaya Diop
(74) *Attorney, Agent, or Firm* — David B. Tingey; Bryant J. Keller; Kirton McConkie

(57) ABSTRACT

A device for the treatment of esophageal stenoses, including at least a body of elongated shape intended to be inserted within the esophagus of a patient, and a tubular sheath mounted around said body to define an interspace between said body and the tubular sheath, wherein it includes a stiffening element accommodated in said interspace and including a plurality of ribs which extend along said interspace.

7 Claims, 2 Drawing Sheets

(51) Int. Cl.
*A61M 29/02* (2006.01)
*A61M 29/00* (2006.01)
*A61M 25/06* (2006.01)

(52) U.S. Cl.
CPC ............ *A61M 29/00* (2013.01); *A61M 29/02* (2013.01); *A61F 2002/044* (2013.01); *A61M 2025/0059* (2013.01); *A61M 2025/0681* (2013.01); *A61M 2205/0216* (2013.01)

(58) Field of Classification Search
CPC ........ A61M 25/005; A61M 2205/0216; A61M 2025/0059; A61M 2025/0681
See application file for complete search history.

(56) References Cited

U.S. PATENT DOCUMENTS

2013/0018318 A1* 1/2013 Ravichandran ... A61M 25/0012
604/172
2013/0158471 A1* 6/2013 Neel ................... A61M 1/0084
604/35

OTHER PUBLICATIONS

International Search Report and Written Opinion dated Sep. 15, 2015 from International Patent Application No. PCT/IB2015/054242 filed Jun. 4, 2015.

* cited by examiner

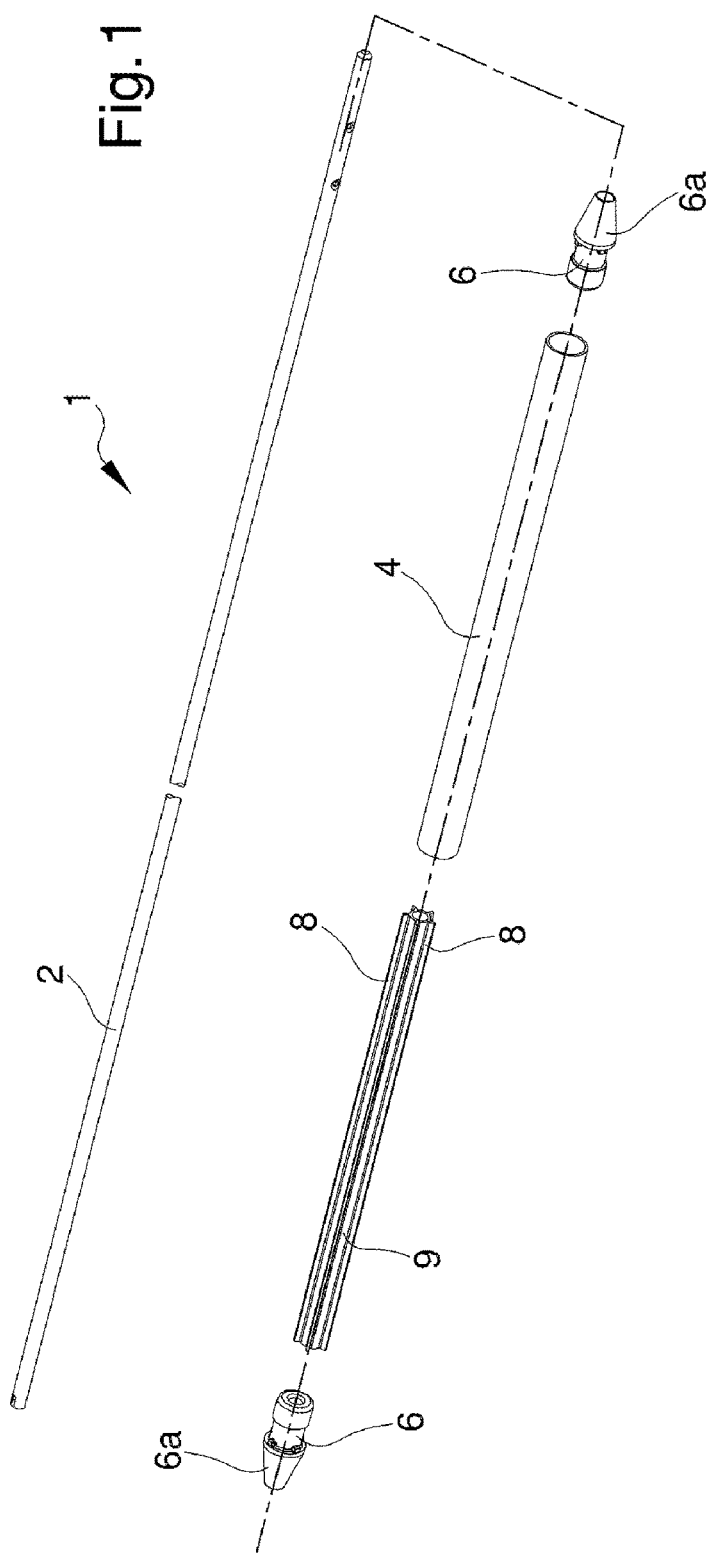
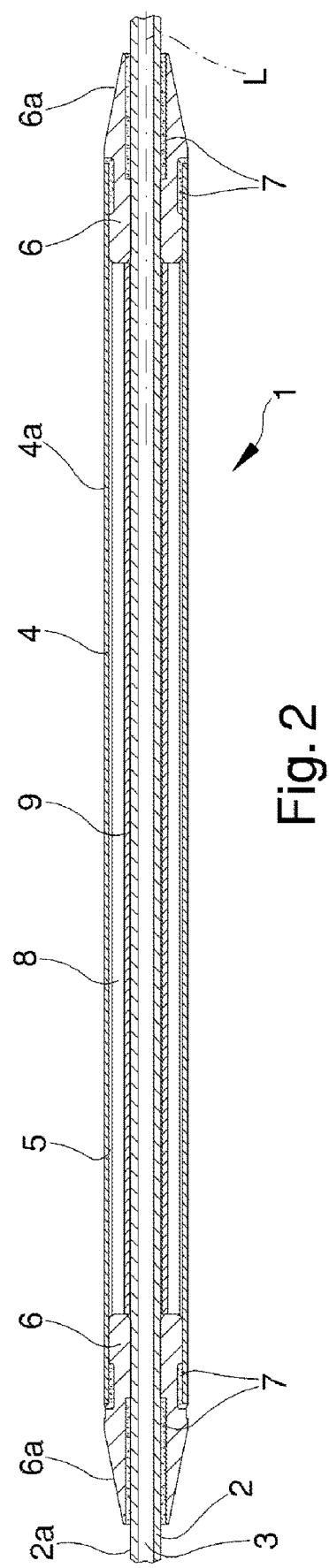

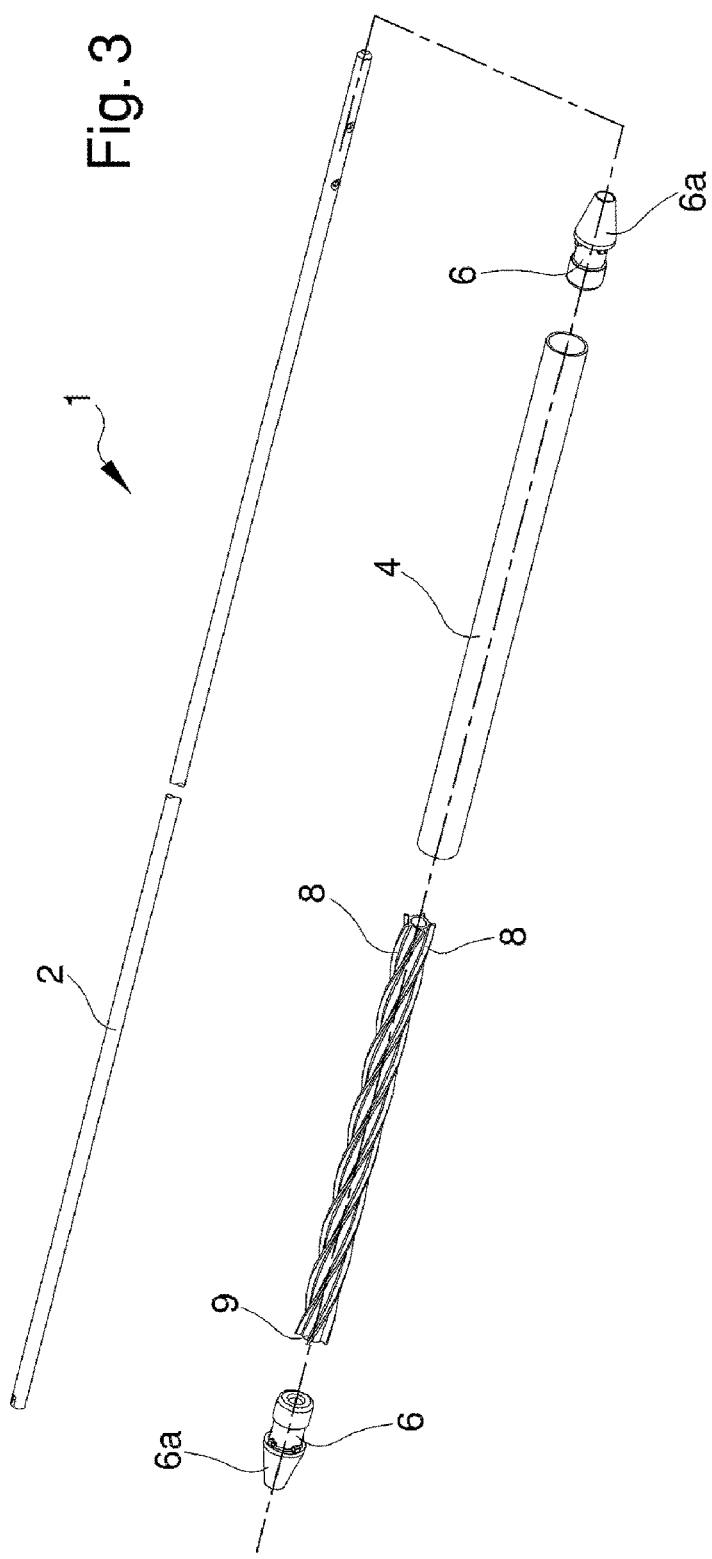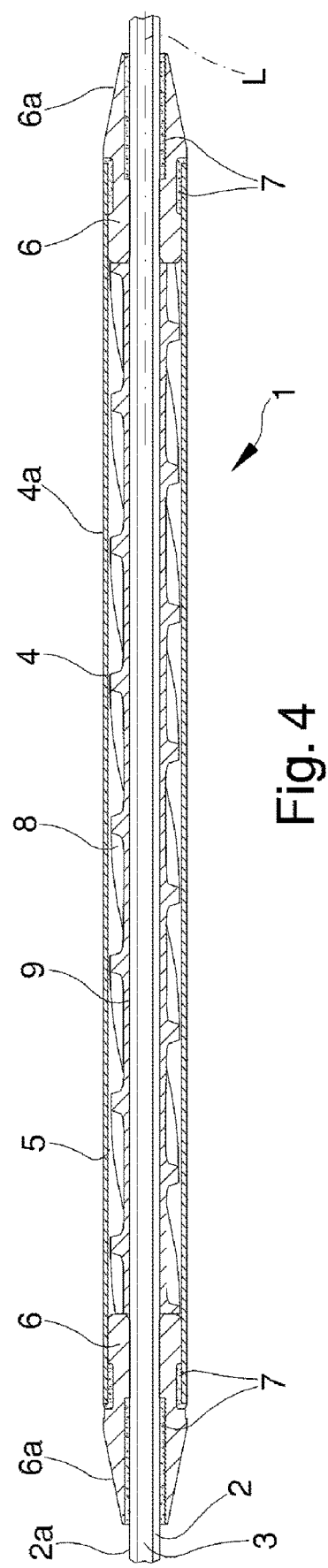

DEVICE FOR THE TREATMENT OF ESOPHAGEAL STENOSES

TECHNICAL FIELD

The present invention relates to a device for the treatment of esophageal stenoses.

BACKGROUND ART

As is known, esophageal stenoses may be caused by a variety of factors such as, e.g., lesions caused by the ingestion of caustic substances, scarring as a result of esophageal anastomosis due to atresia, post-chemotherapy or radiotherapy or peptic lesions, etc.

To allow the resumption of the proper functioning of the organ, thus ensuring the patient a good quality of life, intervention generally involves dilating the tract of the esophagus affected by stenosis.

These dilations must be repeated over time to cope with the inevitable occurrence of relapses.

In order to avoid an excessive number of dilations, appropriate devices are used, also called "removable stents".

The devices of known type used to dilate the esophageal tract affected by the stenosis can be of two types: of the self-expandable type or to be introduced after dilation of the stenosis.

The self-expandable-type devices are able to compress the inner walls of the esophageal tract affected by stenosis, thus preventing the restenosis, and have the characteristic of passing the food inside them.

This type of devices does not however allow restoring, as a result of their removal, a sufficiently wide caliber of the esophagus and above all do not allow same to recover the elasticity necessary to ensure the proper and independent functioning of the organ.

The second type of known devices described above is able, however, to make the food transit around the stent, or between its outer wall and the inner wall of the esophagus.

In particular, the use of this type of devices is aimed at forcing the esophagus to continuously dilate in order to obtain a wider caliber of the esophagus and, above all, greater elasticity.

This type of known devices is not however without drawbacks.

In fact, the food that transits between the device and the wall of the esophagus can both find it hard to transit and inflame or irritate the esophagus itself because of the limited space available and its low elasticity.

This drawback, together also with the sensation of retrosternal encumbrance felt by the patient, may occur especially in periods immediately following the introduction of the device into the esophagus, as a result of the applied dilation. The use of these known devices can therefore be stressful for the patient and for the esophagus itself, and aggravate a clinical situation which is already delicate, with consequent suffering for the patient.

From the patent document WO 2012/110891 a special stent is instead known that has the characteristic of having a central tube, around which the food transits as in the case of the second type of devices referred to above, and variable stiffness means externally associated with the central tube.

The variable stiffness means consist, in particular, of a flexible element, of tubular shape, associated with the central tube so as to define an air chamber interposed between them and fellable with a work fluid.

The stent shown in WO 2012/110891 is however also susceptible to improvements aimed, in particular, at simplifying the device and making it cheaper while maintaining a considerable practicality and efficiency of use.

DESCRIPTION OF THE INVENTION

The main aim of the present invention is to provide a device which allows to overcome the drawbacks of the prior art.

In particular, the present invention aims at providing a device which allows making the food transit between the device itself and the inner walls of the esophagus and which at the same time does not cause any discomfort for the patient.

In particular, the present invention aims at minimizing the risk of irritation or lesions in the esophagus due to the presence of the device itself.

Within this aim, one object of the present invention is to provide a device that can be adapted to the specific conditions of the patient, so as to better optimize the applied therapy and at the same time not lead to any kind of additional discomfort for the patient, thus facilitating full recovery.

Another object of the present invention is to provide a device which can be applied to the patient more easily compared to a device of known type.

Another object of the present invention is to provide a device for the treatment of esophageal stenoses which allows to overcome the mentioned drawbacks of the prior art within the ambit of a simple, rational, easy, effective to use and affordable solution.

The objects stated above are achieved by the present device for the treatment of esophageal stenoses, having the characteristics of claim 1.

BRIEF DESCRIPTION OF THE DRAWINGS

Other characteristics and advantages of the present invention will become more evident from the description of some preferred but not exclusive embodiments of a device for the treatment of esophageal stenoses, illustrated by way of an indicative, but non-limiting, example in the accompanying drawings, in which:

FIG. 1 is an exploded view of a first embodiment of the device according to the invention;

FIG. 2 is a longitudinal section view of the device of FIG. 1;

FIG. 3 is an exploded view of a second embodiment of the device according to the invention;

FIG. 4 is a longitudinal section view of the device of FIG. 3.

EMBODIMENTS OF THE INVENTION

With particular reference to such figures, the reference number 1 generally designates a device for the treatment of esophageal stenoses.

The device 1 comprises at least a body 2 of elongated shape, intended to be inserted within the esophagus of a patient at the tract affected by stenosis to be treated.

The body 2, in particular, extends along a longitudinal direction L and is made of a material sufficiently flexible to allow introduction into the patient through the oral route.

In the embodiments represented in the illustrations, the body 2 has a substantially circular section and is internally hollow to define an inner duct 3.

Around the body 2 is mounted at least a tubular sheath 4 having greater inner diameter that the outer diameter of the body 2 so as to define an interspace 5 between the body 2 and the tubular sheath 4.

Preferably, the tubular sheath 4 also has a circular section and is arranged substantially coaxial to the body 2; the interspace 5 thus has a substantially annular shape.

The device 1 comprises at least a connection element 6 placed between the body 2 and the tubular sheath 4.

The connection element 6 is shaped so as to connect the outer surface 4a of the tubular sheath 4 to the outer surface 2a of the body 2.

More in detail, the connection element 6 defines a coupling surface 6a substantially inclined with respect to the outer surface 4a of the tubular sheath 4 and to the outer surface 2a of the body 2.

Such coupling surface 6a is able to facilitate the transit of food into the space between the device 1 and the inner wall of the esophagus.

Usefully, the device 1 comprises at least two connection elements 6 arranged at the axial ends of the tubular sheath 4.

Each of these two connection elements 6, arranged therefore on opposite sides of the tubular sheath 4, has a respective substantially conical coupling surface 6a.

More in particular, the coupling surfaces 6a of the connection elements 6 converge towards the outside and have an inclination opposite one another, i.e., specular.

The connection elements 6 delimit axially the interspace 5 placed between the body 2 and the tubular sheath 4; it results therefore that the interspace 5 is delimited internally by the body 2, externally by the tubular sheath 4 and axially by the connection elements 6.

The sealed fixing between the connection elements 6, the body 2 and the tubular sheath 4 is ensured by the interposition of an adhesive substance 7, e.g., of the silicone paste type and for example applied between the outer surface 2a of the body 2 and the inner surface of the connection elements 6, as well as between the inner surface of the tubular sheath 4 and the outer surface of the connection elements 6.

According to the invention the device 1 comprises at least a stiffening element 8, 9 accommodated in the interspace 5 and comprising a plurality of ribs 8 which extend along the interspace 5.

In the particular embodiment shown in FIGS. 1 and 2, for example, the ribs 8 are rectilinear and parallel to the longitudinal direction L of the body 2.

In the embodiment shown in FIGS. 3 and 4, on the other hand, the ribs 8 are helical shaped and wound in a spiral fashion around the body 2.

Compared to the embodiment shown in FIGS. 1 and 2, that of FIGS. 3 and 4 has the advantage of stiffening the device 1 in a more balanced manner on all 360° of the circumference of the tubular sheath 4.

In the two embodiments shown in the figures, the stiffening element 8, 9 also comprises a tubular section 9 having an inner surface which can be fitted around the body 2 and an outer surface on which the ribs 8 are arranged.

In other words, in the stiffening element 8, 9 shown in the illustrations, the tubular section 9 is internal and goes to rest on the body 2, while the ribs 8 are external, protruding overhanging from the tubular section 9 and support the tubular sheath 4 when this is crushed by the internal walls of the esophagus. Alternative embodiments cannot however be ruled out wherein the stiffening element 8, 9 comprises a tubular section having an outer surface able to fit within the tubular sheath 4 and an inner surface on which the ribs 8 are arranged.

In this case, the tubular section 9 is external and supports the tubular sheath 4, while the ribs 8 are internal and rest on the body 2.

Other embodiment are also possible in which the stiffening element 8, 9 and the tubular sheath 4 are made in a single monolithic body comprising a tubular section having an outer surface adapted to define the tubular sheath 4 and an inner surface on which the ribs 8 are arranged.

Conveniently, the stiffening element 8, 9 is made of an elastomeric material of predetermined hardness, preferably thermoplastic polyurethane (TPU) of which there is a wide range of products on the market that differ in terms of their physical and mechanical properties such as hardness, modulus of elasticity, strength, etc.

In practice, it is possible to place at the disposal of the physician who is treating the patient a set of devices 1 with differentiated rigidity, from among which is chosen that which, not only in terms of size but also of stiffness, is best suited to use and offers the best resistance to the transit of food through the esophagus, according to the real conditions of the patient and of the progress of the rehabilitation therapy.

Finally, the device 1 also comprises one or more radiopaque markers, not shown in detail in the illustrations, able to allow the identification from the outside of the exact position of the device itself within the esophagus.

These markers can be positioned inside the walls of the body 2, of the connection elements 6 and of the stiffening element 8, 9, or, alternatively, can be housed in a portion of the interspace 5 or drowned in the interstices between the connection elements 6 and the body 2 or between the connection elements 6 and the stiffening element 8, 9.

The operation of the device according to the invention is the following.

The device 1 is applied to the patient by means of a known technique which provides for the insertion, using the work channel of a previously-used endoscope, of a rigid type guide wire.

After extracting the endoscope and performing the dilations with appropriate technique of the tract of esophagus affected by stenosis, the device 1 is made to advance along the guide wire and its position is controlled by means of appropriate radiological instruments which allow viewing the radiopaque markers mounted on the device itself.

The extremity of the device 1 which emerges from the oral cavity is then made to transit in the retropharynx and to come out of a nostril.

The position of the body 2 within the esophagus can, e.g., be blocked by applying to the patient a nasogastric tube, of a type known in itself.

It has in practice been ascertained how the described invention achieves the proposed objects and in particular the fact is underlined that the present device for the treatment of esophageal stenoses, thanks to the presence of the stiffening element provided with ribs, permits exerting an effective action throughout the period in which it is applied to the patient, while at the same time reducing the pain suffered by the patient him/herself.

In particular, the present invention allows the user to make the food transit between the device and the inner walls of the esophagus and at the same time does not cause any discomfort at all for the patient, thus facilitating his/her full recovery without irritating or injuring the esophagus.

The invention claimed is:

1. A device for treatment of esophageal stenoses, comprising:
   a body of elongated shape configured to be inserted within an esophagus of a patient;
   a tubular sheath mounted around said body to define an interspace between said body and said tubular sheath;
   a stiffening element accommodated in said interspace and comprising a plurality of ribs which extend along said interspace;
   a first connection element coupled to a first axial end of said tubular sheath, wherein said first connection element comprises a taper from said first axial end of said tubular sheath to an end of said first connection element; and
   a second connection element coupled to a second axial end of said tubular sheath,
   wherein said second connection element comprises a taper from said second axial end of said tubular sheath to an end of said second connection element,
   wherein at least one of said first connection element and said second connection element is coupled to said body and delimits axially said interspace, and
   wherein said plurality of ribs are helical shaped and wound in a spiral around said body.

2. The device according to claim 1, wherein said stiffening element is comprises an elastomeric material of predetermined hardness.

3. The device according to claim 1, wherein said stiffening element comprises a tubular section having an inner surface which can be fitted around said body and an outer surface on which said plurality of ribs are arranged.

4. The device according to claim 1, wherein said stiffening element comprises a tubular section having an outer surface which can be fitted within said tubular sheath and an inner surface on which said plurality of ribs are arranged.

5. The device according to claim 1, wherein said stiffening element and said tubular sheath are made in a single monolithic body comprising a tubular section having an outer surface adapted to define said tubular sheath and an inner surface on which said plurality of ribs is arranged.

6. The device according to claim 1, wherein said body has a substantially circular section and said tubular sheath is arranged substantially coaxial to said body.

7. The device according to claim 1, wherein each of said connection elements defines a respective coupling surface inclined with respect to the outer surface of said tubular sheath and to the outer surface of said body.

* * * * *